(12) United States Patent
Wellman et al.

(10) Patent No.: US 6,616,661 B2
(45) Date of Patent: Sep. 9, 2003

(54) SURGICAL DEVICE FOR CLAMPING, LIGATING, AND SEVERING TISSUE

(75) Inventors: Parris S. Wellman, Hillsborough, NJ (US); Kevin S. Weadock, Princeton, NJ (US); Robert Nering, Stockton, NJ (US)

(73) Assignee: Ethicon, Inc., Somervillle, NJ (US)

( * ) Notice: Subject to any disclaimer, the term of this patent is extended or adjusted under 35 U.S.C. 154(b) by 0 days.

(21) Appl. No.: 09/967,204

(22) Filed: Sep. 28, 2001

(65) Prior Publication Data

US 2003/0065326 A1 Apr. 3, 2003

(51) Int. Cl.[7] ................................. A61B 17/32
(52) U.S. Cl. ............................. 606/50; 606/48; 606/45; 606/51
(58) Field of Search ............................. 606/41, 47, 48, 606/50, 51, 52, 158, 159, 167, 170

(56) References Cited

U.S. PATENT DOCUMENTS

| | | |
|---|---|---|
| 5,403,312 A | 4/1995 | Yates et al. |
| 5,573,535 A | 11/1996 | Viklund |
| 6,019,771 A * | 2/2000 | Bennett et al. ............. 606/159 |
| 6,110,170 A * | 8/2000 | Taylor et al. ................. 606/49 |
| 6,193,653 B1 * | 2/2001 | Evans et al. ................ 606/170 |
| 6,464,702 B2 * | 10/2002 | Schulze et al. ............... 606/51 |

* cited by examiner

*Primary Examiner*—Linda C. M. Dvorak
*Assistant Examiner*—David M. Ruddy (57) ABSTRACT

A surgical device for severing tissue, the surgical device comprising; a first shaft having a first internal lumen and a first slot disposed at a distal end; a clamp slidingly disposed in the first slot between open and closed positions to capture tissue in the first slot, the clamp having a clamping surface disposed at a distal end; at least one electrode for applying RF energy to the tissue captured in the first slot; a cutting blade slidingly disposed in the first slot between open and closed positions, the cutting blade having a cutting edge to sever the tissue; first actuation means for actuating the clamp between the open and closed positions; and second actuation means for actuating the cutting blade between the open and closed positions.

20 Claims, 4 Drawing Sheets

SURGICAL DEVICE FOR CLAMPING, LIGATING, AND SEVERING TISSUE

BACKGROUND OF THE INVENTION

1. Field of the Invention

The present invention relates generally to surgical devices, and more particularly, to a surgical device for clamping, ligating, and severing tissue, preferably, a side branch of a vessel to be harvested.

2. Prior Art

Both saphenous veins and radial arteries are used as conduits in coronary artery bypass surgery. Conventional techniques for harvesting these vessels involve an incision length approximately equal to the length of the vessel being harvested. Recently, various bipolar endoscopic vessel-harvesting devices have been developed as a means of removing saphenous veins or radial arteries in a minimally invasive manner.

Users of theses devices frequently struggle to separate side branches of the veins or arteries when said side branches run beneath or above the main trunk of the vessel. In addition, the visualization of the vessel may be lost in excess adipose tissue. Finally, the user friendliness of these devices is subject to question since the steps involved in identifying, securing, and dissection/ligation of side branches is not always intuitive, i.e., the user frequently has to concentrate on what his or her hands are doing and not the vessel at hand. Current bipolar devices also fail to complete the terminal ligation required to excise the vein or artery.

Others have attempted to harvest vessels via endoscopic means by several methods. One method involves use of scissors and ligating clips. Two tools are required for this approach, thus complicating the procedure by excess tool exchanges. Furthermore, the placed clips can hinder subsequent movement of instruments. Finally, foreign bodies (clips) are left in the patient's limb.

Another approach involves the use of a knife placed between two wire guides that are capable of applying a current across the side branch. This design can potentially result in the spread of thermal energy to the target vessel, potentially compromising its utility as a conduit for CABG surgery. Still yet another approach involves the use of scissor-like clamping jaws that open around a side branch, and then must be closed, whereby a current is applied to the vessel within the jaws before the vessel is harvested. However, these types of instruments are difficult to use in confined spaces because of the upward opening movement of at least one of the jaws often causes an interference with objects in the field. Further, the upward opening jaw obscures the vision of the surgeon using the device.

SUMMARY OF THE INVENTION

Therefore it is an object of the present invention to provide a surgical device for clamping, ligating, and severing tissue, which is friendlier to use than the devices of the prior art.

It is another object of the present invention to provide a surgical device for clamping, ligating, and severing tissue, which eliminates the need for ligating clips to ligate side branches of a vessel being harvested.

It is yet another object of the present invention to provide a surgical device for clamping, ligating, and severing tissue which limits the spread of thermal energy so as not to compromise the utility of the vessel to be harvested.

It is yet another object of the present invention to provide a surgical device for clamping, ligating, and severing tissue which eliminates the necessity of opening and closing scissor-like jaws.

It is still yet another object of the present invention to provide a surgical device for clamping, ligating, and severing tissue, which minimizes the need for multiple instrument exchanges needed to harvest a vessel.

Accordingly, a surgical device for severing tissue is provided. The surgical device comprising; a first shaft having a first internal lumen and a first slot disposed at a distal end; a clamp slidingly disposed in the first slot between open and closed positions to capture tissue in the first slot, the clamp having a clamping surface disposed at a distal end; at least one electrode for applying RF energy to the tissue captured in the first slot; a cutting blade slidingly disposed in the first slot between open and closed positions, the cutting blade having a cutting edge to sever the tissue; first actuation means for actuating the clamp between the open and closed positions; and second actuation means for actuating the cutting blade between the open and closed positions. The tissue is preferably a side branch of a vessel being harvested. Preferably, the first shaft is disposed at a proximal end to a handle.

The surgical device preferably further comprising a dissection tip disposed at the distal end of the first shaft for dissecting tissue.

The clamp preferably comprises a second shaft having a second internal lumen, the second shaft being slidingly disposed in the first lumen. More preferably, the second shaft has a second slot at the distal end, wherein the second slot divides the clamping surface into two prongs. The cutting blade is preferably slidingly disposed in the second internal lumen of the second shaft. Preferably, the at least one electrode comprises first and second electrodes, each of a different polarity. More preferably, the first electrode comprises at least the clamping surface of the clamp and the second electrode comprises at least the cutting edge of the cutting blade. Alternatively, the first electrode comprises at least the clamping surface of the clamp and at least the cutting edge of the cutting blade and the second electrode comprises at least a portion of the first shaft. The at least a portion of the first shaft preferably comprises an edge defining the first slot in the first shaft.

Preferably, the first actuation means comprises a button movably disposed in a handle and operatively connected to the clamp, wherein moving the button moves the clamp between the open and closed positions. The second actuation means preferably comprises a button movably disposed in a handle and operatively connected to the cutting blade, wherein moving the button moves the cutting blade between the open and closed positions. More preferably, the first and second actuation means comprises a button movably disposed in a handle and operatively connected to the clamp and cutting blade, wherein moving the button a first predetermined amount moves the clamp between the open and closed positions and moving the button a second predetermined amount further moves the cutting blade between the open and closed positions.

Also provided is a method for severing tissue with the surgical devices of the present invention. The method comprising: capturing tissue in the first slot; sliding the clamp in the first slot to clamp the tissue in the first slot; applying RF energy to the at least one electrode to cauterize the tissue; sliding the cutting blade in the first slot to sever the cauterized tissue. The tissue is preferably a side branch of a vessel to be harvested.

The method preferably further comprising dissecting tissue from the vessel to be harvested. Preferably, the first actuation means comprises a button movably disposed in a handle and operatively connected to the clamp, the method further comprising moving the button to move the clamp between the open and closed positions. Preferably, the second actuation means comprises a button movably disposed in a handle and operatively connected to the cutting blade, the method further comprising moving the button to move the cutting blade between the open and closed positions. More preferably, the first and second actuation means comprises a button movably disposed in a handle and operatively connected to the clamp and cutting blade, the method further comprising moving the button a first predetermined amount to move the clamp between the open and closed positions and moving the button a second predetermined amount to further move the cutting blade between the open and closed positions.

BRIEF DESCRIPTION OF THE DRAWINGS

These and other features, aspects, and advantages of the apparatus and methods of the present invention will become better understood with regard to the following description, appended claims, and accompanying drawings where:

DETAILED DESCRIPTION OF THE PREFERRED EMBODIMENT

Although this invention is applicable to numerous and various types of tissue to be severed, it has been found particularly useful in the environment of severing vessels such as side branches of a blood vessel being harvested. Therefore, without limiting the applicability of the invention to severing vessels such as side branches of a blood vessel being harvested, the invention will be described in such environment. Furthermore, the surgical devices of the present invention are preferably configured as disposable devices, however, the surgical devices can also be configured as semi-reusable or reusable without departing from the scope or spirit of the present invention.

Figure 1:
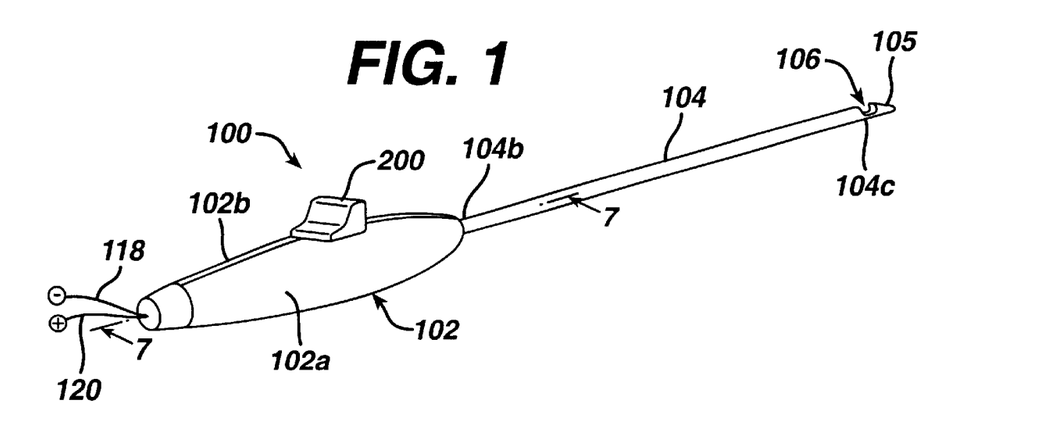
FIG. 1 illustrates an isometric view of a preferred implementation of a surgical device of the present invention.
Figure 7:
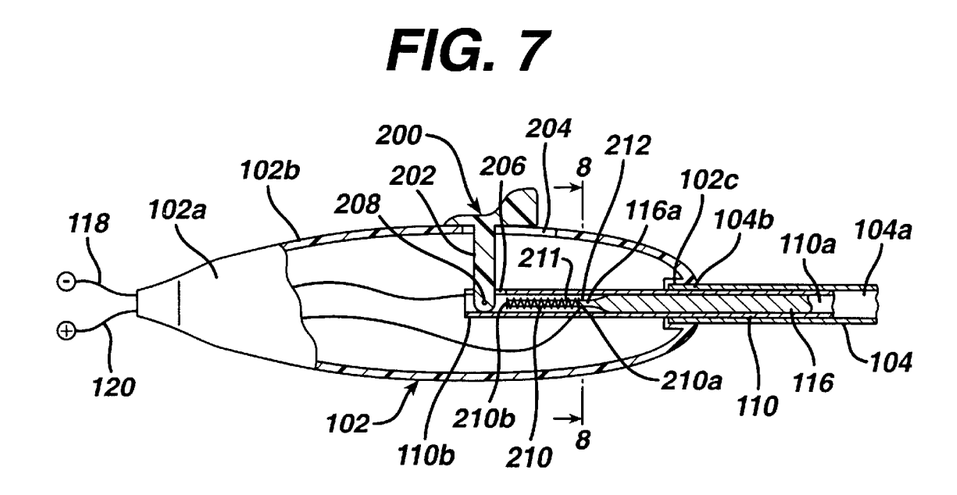
FIG. 7 illustrates a sectional view of the surgical device taken along line 7—7 of FIG. 1.

Referring now to FIGS. 1 and 7, a surgical device is illustrated therein, generally being referred to by reference numeral 100. The surgical device 100 has a housing 102, also serving as, and alternatively referred to as a handle. The handle 102 is generally fabricated from a medical grade thermoplastic and is preferably formed in a "clamshell" design having first and second halves 102a, 102b. The clamshell design allows for easy assembly of the internal components. The halves 102a, 102b are fixed together by any means known in the art, such as by a press fit or with a medical grade epoxy.

The surgical device 100 further has a first shaft 104 having a first internal lumen 104a. The first shaft is fabricated from a medical grade resilient material such as stainless steel and preferably has a proximal end 104b affixed to a distal end 102c of the handle 102 by any means known in the art such as a press fit or with a medical grade epoxy.

Figure 2:
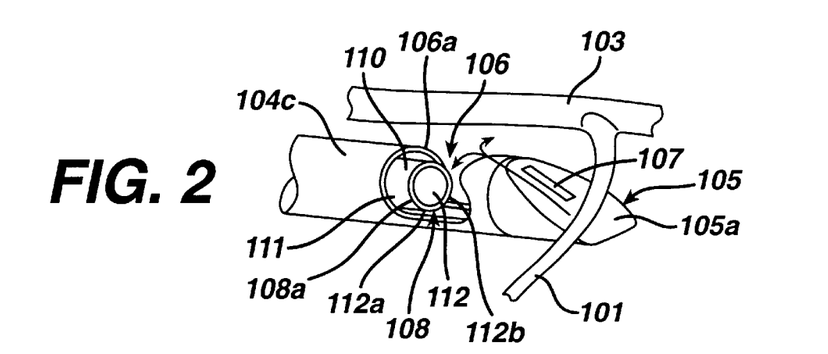
FIG. 2 illustrates an enlarged view of the distal end of the surgical device of FIG. 1.
Figure 3:
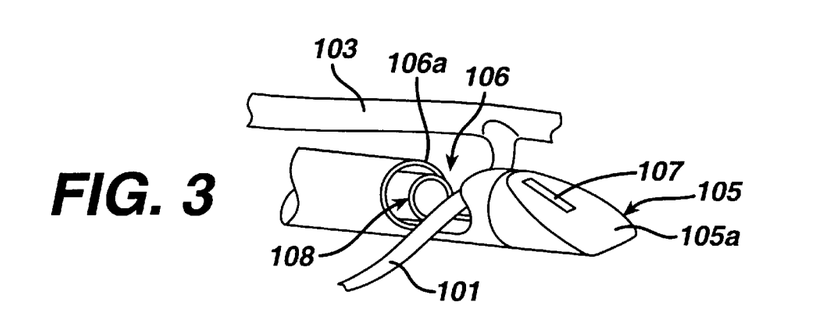
FIG. 3 illustrates the distal end of FIG. 2, wherein a vessel in captured in a slot of the surgical device.

Referring now to FIGS. 1—3, a slot 106 is disposed at a distal end 104c of the first shaft 104. The slot 106 is preferably formed by removing material from a cross-sectional portion of the first shaft 104 such that the slot 106 has a peripheral edge 106a defining the boundaries of the slot 106. The removal of material to form the slot 106 can be done by conventional machining or punching processes known in the art. The slot 106 is shown encompassing a large portion of the cross-section of the first shaft 104 so as to accommodate the largest size tissue 101 possible for a given diameter first shaft 106.

The surgical device 100 further includes a clamp 108 slidingly disposed in the slot 106 between open and closed positions to capture tissue 101, such as a vessel, in the slot 106. As discussed above, the vessel is preferably a side branch 101 of a vessel 103 to be harvested. The clamp 108 further has a clamping surface 108a disposed at a distal end of the clamp 108. In the open position, the clamp 108 does not substantially interfere with the capturing of tissue in the slot 106, while in the closed position, the clamp 108 captures tissue between the clamping surface 108a and at least a portion of the slot edge 106a, preferably a distal portion of the slot edge 106a.

Preferably, the clamp 108 comprises a second shaft 110 having a second internal lumen 110a. The second shaft 110 is slidingly disposed in the first lumen 104a of the first shaft 104. The second shaft 110 is preferably a resilient medical grade material such as stainless steel and preferably a loose running fit is maintained between the first shaft 104 and the second shaft 110. Alternatively, a spacer (not shown) can be provided between the first shaft 104 and the second shaft 110, to define an annular space (not shown) between the first shaft 104 and the second shaft 110. The spacer is preferably a polymer. The polymer spacer can also act as a dielectric insulator. Still more preferably, the second shaft 110 has a slot 112 extending axially from a distal end 111 of the second shaft 110. Preferably, the slot 112 divides the clamping surface 108a into two discrete portions or prongs 112a, 112b.

Figure 4:
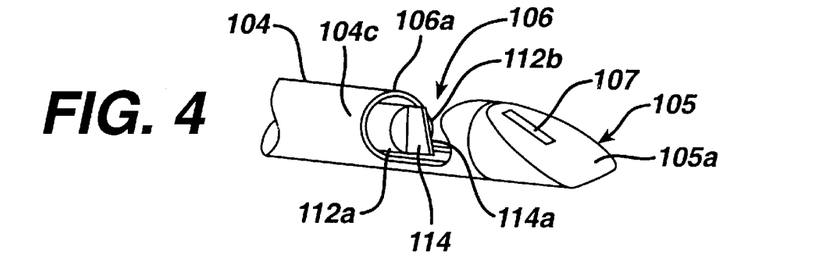
FIG. 4 illustrates the distal end of FIG. 2 with a cutting blade partially extended into the slot.
Figure 5:
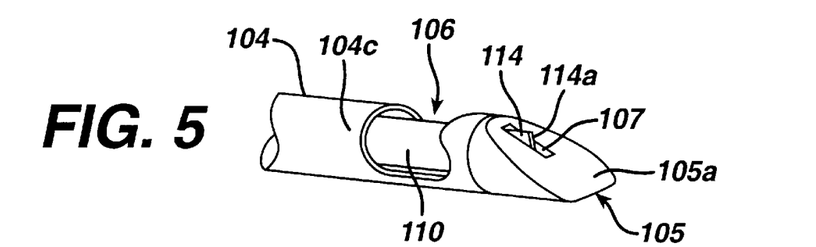
FIG. 5 illustrates the distal end of FIG. 2 with the cutting blade extended fully through the slot.

Referring now to FIGS. 4, 5, and 7, the surgical device 100 also has a cutting blade 114 slidingly disposed in the first slot 106 between open and closed positions. The cutting blade 114 preferably has a sharpened leading cutting edge 114a. In the open position, the cutting blade 108 does not substantially interfere with the capturing of tissue in the slot 106, while in the closed position, the cutting blade 114 severs the captured tissue between the clamping surface 108a and at least a portion of the slot edge 106a.

The cutting blade 114 is preferably at a distal end of a third shaft 116, which is slidingly disposed in the second internal lumen 110a of the second shaft 110. The third shaft 116 is preferably a resilient medical grade material such as heat-treatable stainless steel and preferably a loose running fit is maintained between the third shaft 116 and the second shaft 110. Alternatively, a spacer (not shown) can be provided between the third shaft 116 and the second shaft 110 to define an annular space (not shown) between the second shaft 110 and the third shaft 116. The spacer is preferably a polymer. The polymer spacer can also act as a dielectric insulator. At least the cutting edge 114a of the cutting blade 114 is preferably heat treated to maintain a sharp edge for the expected life of the surgical device 100.

At least one electrode is provided on the surgical device 100 for applying RF energy to the tissue captured in the slot 106. Preferably, the surgical device 100 is configured to apply RF energy to cauterize the captured tissue and more preferably, the surgical device 100 is further configured as a bipolar device. However, the preferable means for cauterization is given by way of example only and not to limit the scope or spirit of the present invention. For instance, the surgical device 100 can be used in a monopolar configuration in combination with a grounding plate as is known in the art. Furthermore, the surgical device 100 can be configured to apply sonic energy to cauterize the captured tissue.

In the preferred bipolar configuration, the at least one electrode comprises first and second electrodes, each of a different polarity. Preferably, the first electrode comprises at least the clamping surface 108a of the clamp 108 and the second electrode comprises at least the cutting edge 114a of the cutting blade 114. Alternatively, the first electrode comprises at least the clamping surface 108a of the clamp 108 and at least the cutting edge 114a of the cutting blade 114 and the second electrode comprises at least a portion of the first shaft 104. In the alternative configuration, the at least a portion of the first shaft 104 comprises the edge 106a defining the slot 106.

The RF energy is preferably supplied from an electrosurgical generator (not shown), as is known in the art. The electrosurgical generator supplies the RF energy to the respective electrodes via wires 118, 120. The wires 118, 120 are preferably routed through the handle 102 and electrically coupled, such as by soldering, to the respective electrodes. A switch (not shown) is also preferably provided for energizing the electrodes with RF energy from the electrosurgical generator. The switch (not shown) can be provided in the handle 102 or in a foot switch as are known in the art.

In either bipolar configuration, surfaces such as the exterior of the first, second, and/or third shafts 102, 110, 116 must be coated with a dielectric material to prevent a short between the electrodes of different polarity and also to prevent accidental cauterization of unintended tissue. Such coatings are well known in the art, such as polytetrafluoroethylene (PTFE). It is important to note, that because the electrodes are offset from one another, thermal spread to unintended portions of the tissue or vessel being cauterized is minimized.

Figure 8:
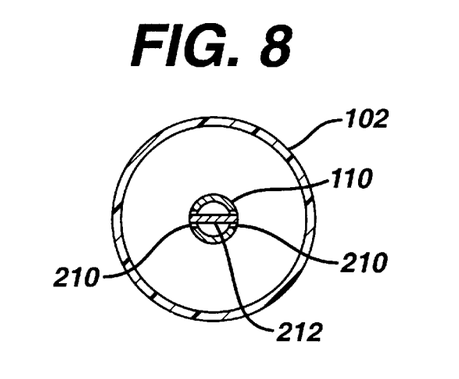
FIG. 8 illustrates a sectional view taken along line 8—8 of FIG. 7.

Referring now to FIGS. 7 and 8, the surgical device 100 also includes first actuation means for actuating the clamp 108 between the open and closed positions. In addition to the first actuation means, the surgical device 100 further includes second actuation means for actuating the cutting blade 114 between the open and closed positions. Preferably, the first and second actuation means are provided by actuation of a single button 200 movably disposed in the handle 102. The button 200 is preferably movably disposed in the handle 102 and operatively connected to both the clamp 108 and cutting blade 114, wherein moving the button 200 a first predetermined amount moves the clamp 108 between the open and closed positions and moving the button 200 a second predetermined amount further moves the cutting blade 114 between the open and closed positions.

Preferably, the button 200 includes a button projection 202 either integral with or separably attached to the button 200. The button projection 202 is slidingly disposed in a slot 204 in the handle 102. A portion of the button projection is disposed in a first slot 206 in a proximal end 110b of the second shaft 110 and connected thereto, preferably by a pinned joint 208. The first slot preferably extends in the axial direction from the distal-most end of the second shaft 110. Thus, since the button 200 and second shaft 110 are directly linked, a distal movement of the button 200 results in a corresponding distal movement of the second shaft 110 and clamp 108 attached at a distal end thereof. The second shaft 110 can be biased in either of the closed or open positions by way of a spring (not shown) disposed in the handle 102.

The second shaft 110 preferably further has a second slot 210 formed at the proximal end 110b in a wall of the second shaft 110 and extending in the axial direction. Preferably, the second slot 210 is formed at two sides of the wall of the second shaft 110. The third shaft 116 has a pin 212, either integrally formed or separably attached, at a proximal end 116a of the third shaft. The pin is slidingly disposed in a distal end 210a of the second slot 210 when the clamp 108 is in the open position. Thus, as the button 200 is moved distally to move the clamp 108 towards the closed position, the pin 212 moves in the second slot 210 from the distal end 210a towards a proximal end 210b of the second slot 210. However, during the movement of the pin 212 in the second slot 210, the third shaft 116 and the cutting blade 114 attached thereto are stationary. When the pin 212 reaches the proximal end 210b of the second slot 210, continued distal movement of the button 200 causes the distal end 210b of the second slot 210 to urge against the pin 212 to correspondingly move the third shaft 116 and the cutting blade 114 attached thereto distally from the open to the closed position to sever tissue captured in the clot 106 of the first shaft 104.

Preferably, a spring 211 is disposed in the second slot 210 between the pin 212 and the proximal end 210b of the second slot 210. The spring 211 ensures that the cutting blade 114 will not move into the slot 116 until the clamp 108 is fully through the slot 116. Furthermore, the spring constant of the spring 211 can be chosen such that a sufficient clamping force must be reached before the cutting blade 114 is advanced. This ensures a proper ligation of a vessel 101 captured in the slot 106 before transection by the cutting edge 116 of the cutting blade 114.

Alternatively, two buttons (not shown) can be provided, one of which operates the actuation of the clamp 108 between the open and closed positions and the other of which operates the actuation of the cutting blade 114 between the open and closed positions. Furthermore, a switch (not shown) can be provided to apply the cauterization energy to the electrodes automatically upon the completion of clamping of the tissue and subsequent to the cutting of the cauterized tissue.

Figure 6A:
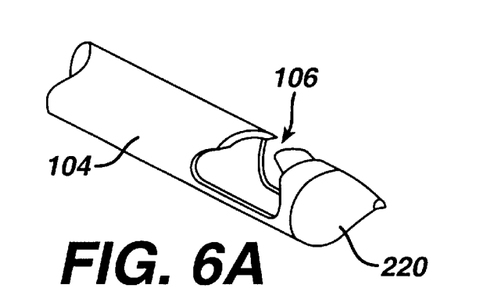
FIGS. 6A, 6b, and 6c illustrate the distal end of FIG. 2 with alternative dissection tips.
Figure 6B:
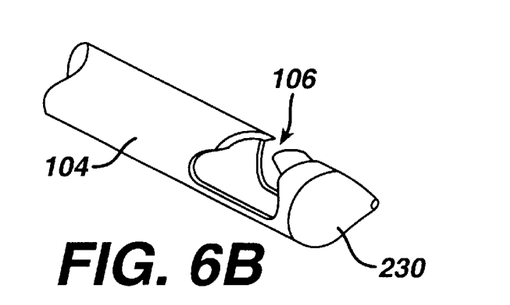
Figure 6C:
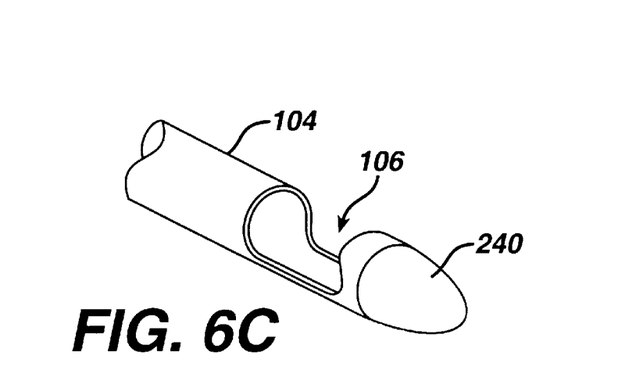

Referring back to FIG. 2, the surgical device 100 also preferably includes a dissection tip 105 disposed at the distal end 104c of the first shaft 104 for dissecting tissue. The dissection tip 105 is preferably separably formed from the first shaft 104 and attached by any means known in the art such as by a press fit, medical grade epoxy, or brazing. However, the dissection tip 105 can also be integrally formed with the first shaft 104, such as by rolling the distal edge 104c of the first shaft 104 into an appropriate shape. The dissection tip is preferably shaped to facilitate the dissection of tissue and further has a sloped leading edge 105a for facilitating capturing of a vessel in the slot 106. The dissection tip 105 further preferably has a slot 107 formed therein for acceptance of a distal portion of the cutting blade 114 as shown in FIG. 5. FIGS. 6A, 6B, and 6C illustrate alternative dissection tips 220, 230, 240, respectively.

Preferably, the surgical device further has a means (not shown) for evacuating smoke or other fluids from the body. Typically, the evacuating means comprises a vacuum port (not shown) such as a luer fitting disposed in the handle 102, which is in fluid communication with at least one of the lumens 104a, 110a of the first and second shafts 104, 110 at one end and connected to a vacuum supply at another end.

Figure 9:
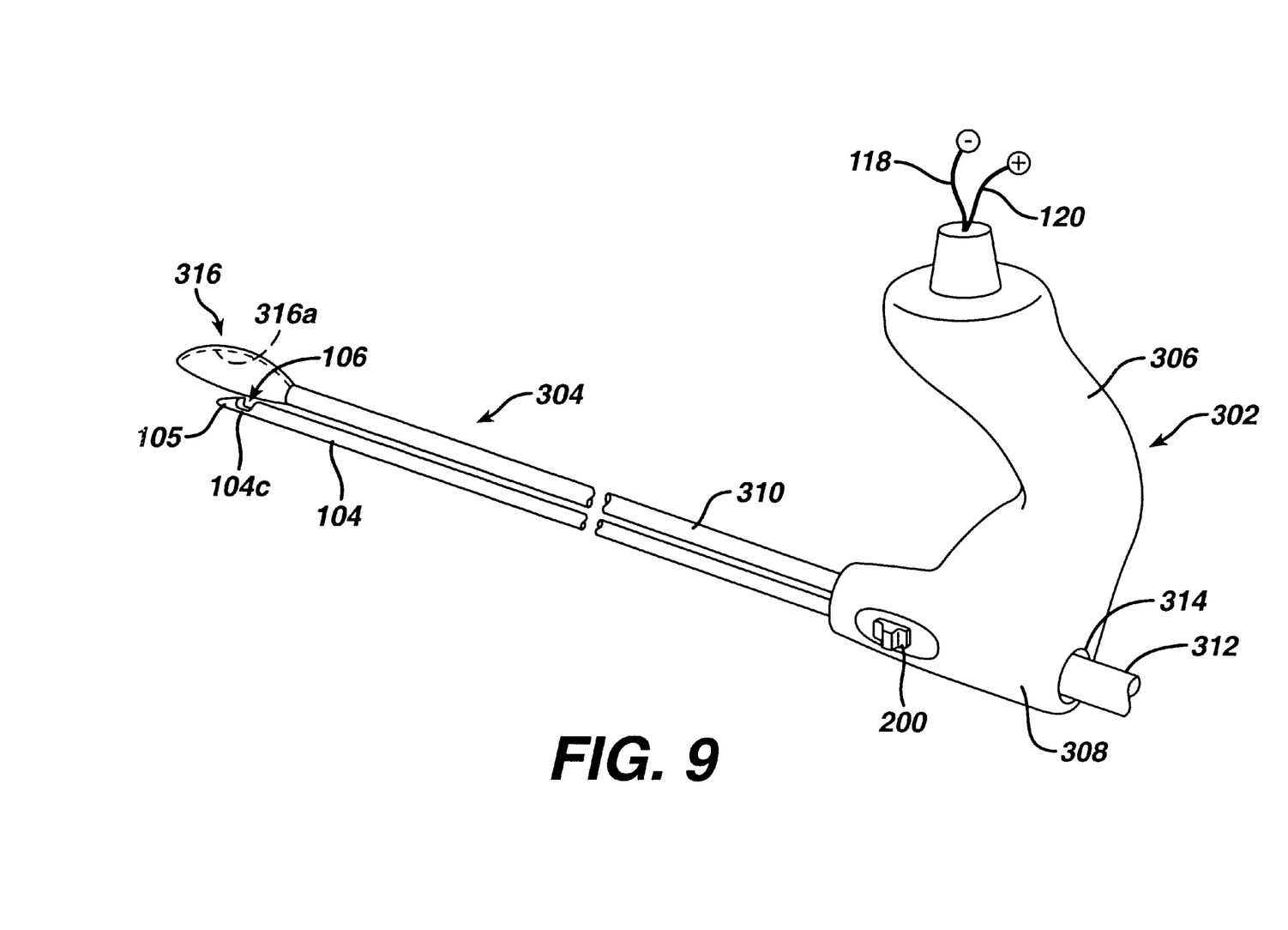
FIG. 9 illustrates a variation of the surgical device of FIG. 1.

Referring now to FIG. 9 where like numbers represent similar components, a variation of the surgical device 100 is illustrated therein. The variation of the surgical device being generally referred to by reference numeral 300. The surgical device 300 illustrated in FIG. 9 is similar to the surgical device 100 illustrated in FIG. 1, but is particularly configured for endoscopic vein harvesting.

The device 300 comprises a substantially similar instrument as disclosed in FIGS. 1–5 and 7–8, with the exception that the housing 302 is configured as is known in the art for blood vessel dissection and although surgical device 100 preferably includes a dissection tip 105, surgical device 300 includes a further dissection means 304 for dissecting tissue from a blood vessel to be harvested. The housing 302 of surgical device 300 is pistol or L-shaped and has a handle portion 306. The housing 302 also has a control portion 308 for placement of the button 200 as well being a housing for the remaining components of the first and second actuation means discussed previously with regard to surgical device 100.

The dissection means 304 preferably comprises a third shaft 310 having an internal lumen for passage of an endoscope 312 therein. The internal lumen communicates with a lumen (not shown) in the handle and has a hole 314 for insertion of the endoscope therein. The third shaft 310 and the first shaft 104 are preferably arranged parallel to one another and each are connected at a proximal end to the control portion 308 of the housing 302.

The dissection means 304 further has a substantially transparent headpiece 316 shaped for dissecting tissue in proximity to the vessel 103. Dissecting tissue about a vessel 103 with such a dissection means 304 is well known in the art, such as that disclosed in U.S. Pat. No. 6,206,823, the contents of which are incorporated herein by its reference. In general, the headpiece 316 is advanced along the vessel 103 to dissect the surrounding tissue from the vessel 103. Furthermore, a workspace is created between an interior surface 316a of the headpiece 316 and the vessel 103 for placement of the distal end 104c of the first shaft 104. If a side branch 101 of the vessel 103 is encountered during the dissection (as viewed by the endoscope), the same is ligated and dissected in the workspace using the clamp 108, electrodes, and cutting blade 114 as is described below.

A method for severing a side branch 101 of a vessel 103 using the surgical devices 100, 300 of the present invention will now be described with reference to the Figures. A vessel 103 to be harvested is first accessed by making an incision, generally in the leg. Next, pre-dissection of an end of the vessel 103 is performed. After pre-dissection, the vessel 103 is traversed and dissected from the surrounding tissue. The dissection of the surrounding tissue can be performed with the dissection tip 105 and/or the dissection means 304. During the dissection of the vessel 103, whenever a side branch 101 is encountered, the device is positioned and advanced such that the side branch 101 rides up the inclined leading edge 105a of the dissection tip 105 until it falls into and is captured in the slot 106 as is shown by arrow A in FIG. 2.

Subsequent to capturing the side branch 101 in the slot 106, the button 200 is advanced distally to slide the clamp 108 in the slot 106 to clamp the side branch 101 in the slot 106. Preferably, the side branch 101 is clamped between the clamping surface 108a and a distal portion of the edge 106a defining the slot 106. Once the side branch 101 is captured, RF energy is preferably applied to the electrodes to cauterize the captured side branch 101. The cauterization of the side branch 101 sufficiently ligates the side branch 101 such that it can be safely severed. The side branch 101 is severed by continuing to advance the button distally which results in the advancement of the cutting blade distally through slot 106 and into slot 107 to sever the cauterized side branch 101. Those skilled in the art will appreciate that because the ligation and transection of the captured tissue or vessel is performed in an open slot 106, visualization is greatly improved, even while the device 100, 300 is being advanced through tissue.

Although, the devices 100, 300 are particularly useful for severing side branches 101 of a vessel 103 to be harvested, they can also be utilized in other procedures such as ligation of fallopian tubes for fertility control, ligation and transection of bile ducts for nephrectomy, or for the transection of ligaments or other tissue structures.

EXAMPLE

As discussed above, the present invention has particular utility in a coronary artery bypass graft procedure (CABG), however, the use of the instruments of the present invention is now described with regard to the CABG procedure by way of example only and not to limit the scope or spirit of the present invention. A patient is prepared for cardiac surgery in a conventional manner using conventional techniques and procedures. The patient is then anesthetized and ventilated using conventional techniques. A conventional CABG procedure is performed by harvesting the greater saphenous vein from one or both of the patient's legs. The surgeon prepares an opening to the heart by dividing the patient's sternum (conventional median sternotomy) and spreading the rib cage apart using a surgical retractor. The surgeon next begins dissecting the internal mammary artery (IMA) from the chest wall of the patient, so that the distal end of the vessel may be anastomosed to the diseased lower anterior descending (LAD) coronary artery on the distal side of a lesion on the septum near the left ventricle of the heart as a source of oxygenated blood. During the surgical procedure, the surgeon optionally elects to have the patient's heart beating to perform a conventional beating heart CABG, although the surgeon has a cardiopulmonary bypass machine (CPB) primed with the patient's blood and available if it is necessary to convert the beating heart procedure into a conventional stopped heart procedure.

The surgeon prepares the heart for attaching the graft vessels by cutting and pulling away the pericardium. After checking the graft vessels for patency, collateral damage and viability, the surgeon prepares to do the anastomoses necessary to bypass the lesions in the coronary arteries. The surgeon sutures the proximal end of each graft vessel to the patient's aorta and the distal end to the diseased coronary artery, distal to the blockage or lesion. The distal end of the LAD is similarly anatomosed to a coronary artery distal to a lesion in a conventional manner. The surgeon checks the bypass grafts for adequate blood flow in a conventional manner, and then completes the remainder of the operation in a conventional manner.

The veins used in the CABG procedure are harvested endoscopically using the vein harvesting instruments of the present invention. Using these instruments, initially the patient's leg is positioned to be slightly bent and is turned to expose the inner leg. A marker is used to show on the skin the location of the vein to be harvested. Then an incision is created on the inner leg near the knee, through the skin and subcutaneous layers. The vein typically lies directly beneath the subcutaneous layers and so a middle portion of the vein is accessed through the incision. After some initial dissection with conventional blunt dissectors around this portion of the vein, a surgical instrument is introduced into the incision. An endoscope provides visualization of the vein and surrounding tissue within the working space inside the head. The instrument is advanced along the vein. Side branches off of the vein are ligated and divided a few millimeters away from the vein, taking great care not to injure the vein in any way. The harvesting procedure continues in this manner until the vein is hemostatically isolated from surrounding tissues and blood supply along the portion to be harvested. Then stab incisions are created through the skin and subcutaneous layers at the distal and proximal ends of the vein, ligation clips are applied, and the vessel is transected in order to remove the vein from the knee incision. Thee harvested vein is prepared for use as grafts in a conventional manner.

While there has been shown and described what is considered to be preferred embodiments of the invention, it will, of course, be understood that various modifications and changes in form or detail could readily be made without departing from the spirit of the invention. It is therefore intended that the invention be not limited to the exact forms described and illustrated, but should be constructed to cover all modifications that may fall within the scope of the appended claims.

What is claimed is:

1. A surgical device for severing tissue, the surgical device comprising;
   a first shaft having a first internal lumen and a first slot disposed at a distal end;
   a clamp slidingly disposed in the first slot between open and closed positions to capture tissue in the first slot, the clamp having a clamping surface disposed at a distal end;
   at least one electrode for applying RF energy to the tissue captured in the first slot;
   a cutting blade slidingly disposed in the first slot between open and closed positions, the cutting blade having a cutting edge to sever the tissue;
   first actuation means for actuating the clamp between the open and closed positions; and
   second actuation means for actuating the cutting blade between the open and closed positions.

2. The device of claim 1, further comprising a dissection tip disposed at the distal end of the first shaft for dissecting tissue.

3. The device of claim 1, wherein the first shaft is disposed at a proximal end to a handle.

4. The device of claim 1, wherein the clamp comprises a second shaft having a second internal lumen, the second shaft being slidingly disposed in the first lumen.

5. The device of claim 4, wherein the second shaft has a second slot at the distal end, wherein the second slot divides the clamping surface into two prongs.

6. The device of claim 5, wherein the cutting blade is slidingly disposed in the second internal lumen of the second shaft.

7. The device of claim 6, wherein the at least one electrode comprises first and second electrodes, each of a different polarity.

8. The device of claim 7, wherein the first electrode comprises at least the clamping surface of the clamp and the second electrode comprises at least the cutting edge of the cutting blade.

9. The device of claim 7, wherein the first electrode comprises at least the clamping surface of the clamp and at least the cutting edge of the cutting blade and the second electrode comprises at least a portion of the first shaft.

10. The device of claim 9, wherein the at least a portion of the first shaft comprises an edge defining the first slot in the first shaft.

11. The device of claim 1, wherein the first actuation means comprises a button movably disposed in a handle and operatively connected to the clamp, wherein moving the button moves the clamp between the open and closed positions.

12. The device of claim 1, wherein the second actuation means comprises a button movably disposed in a handle and operatively connected to the cutting blade, wherein moving the button moves the cutting blade between the open and closed positions.

13. The device of claim 1, wherein the first and second actuation means comprises a button movably disposed in a handle and operatively connected to the clamp and cutting blade, wherein moving the button a first predetermined amount moves the clamp between the open and closed positions and moving the button a second predetermined amount further moves the cutting blade between the open and closed positions.

14. The device of claim 1, wherein the tissue is a side branch of a vessel being harvested.

15. A method for severing tissue, the method comprising:
    providing a surgical device comprising; a shaft having an first internal lumen and a slot disposed at a distal end; a clamp slidingly disposed in the slot between open and closed positions to capture tissue in the slot, the clamp having a clamping surface disposed at a distal end; at least one electrode for applying RF energy to the tissue captured in the slot; a cutting blade slidingly disposed in the slot between open and closed positions, the cutting blade having a cutting edge to sever the tissue; first actuation means for actuating the clamp between the open and closed positions; and second actuation means for actuating the cutting blade between the open and closed positions;
    capturing tissue in the slot;
    sliding the clamp in the slot to clamp the tissue in the slot;
    applying RF energy to the at least one electrode to cauterize the tissue;
    sliding the cutting blade in the slot to sever the cauterized tissue.

16. The method of claim 15, wherein the tissue is a side branch of a vessel to be harvested.

17. The method of claim 16, further comprising dissecting tissue from the vessel to be harvested.

18. The method of claim 16, wherein the first actuation means comprises a button movably disposed in a handle and operatively connected to the clamp, the method further comprising moving the button to move the clamp between the open and closed positions.

19. The method of claim 16, wherein the second actuation means comprises a button movably disposed in a handle and operatively connected to the cutting blade, the method further comprising moving the button to move the cutting blade between the open and closed positions.

20. The method of claim 16, wherein the first and second actuation means comprises a button movably disposed in a handle and operatively connected to the clamp and cutting blade, the method further comprising moving the button a first predetermined amount to move the clamp between the open and closed positions and moving the button a second predetermined amount to further move the cutting blade between the open and closed positions.

* * * * *